US009743867B2

(12) United States Patent
Fujii

(10) Patent No.: US 9,743,867 B2
(45) Date of Patent: Aug. 29, 2017

(54) PULSE OXIMETER

(76) Inventor: Takahiro Fujii, Kobe (JP)

(*) Notice: Subject to any disclaimer, the term of this patent is extended or adjusted under 35 U.S.C. 154(b) by 816 days.

(21) Appl. No.: 13/063,415

(22) PCT Filed: Feb. 24, 2010

(86) PCT No.: PCT/JP2010/053369
§ 371 (c)(1),
(2), (4) Date: Apr. 12, 2011

(87) PCT Pub. No.: WO2011/104888
PCT Pub. Date: Sep. 1, 2011

(65) Prior Publication Data
US 2012/0016219 A1    Jan. 19, 2012

(51) Int. Cl.
A61B 5/1455    (2006.01)
A61B 5/00      (2006.01)

(52) U.S. Cl.
CPC ........ *A61B 5/14552* (2013.01); *A61B 5/6826* (2013.01); *A61B 5/6838* (2013.01)

(58) Field of Classification Search
CPC ............ A61B 5/14551; A61B 5/14552; A61B 5/1455; A61B 5/6826; A61B 5/6838
USPC ....... 600/310, 322, 323, 334, 335, 340, 344, 600/473, 476; 356/41
See application file for complete search history.

(56) References Cited

U.S. PATENT DOCUMENTS 4,685,464 A * 8/1987 Goldberger et al. ......... 600/344
5,258,437 A * 11/1993 Takeuchi et al. ............ 524/405
5,339,810 A * 8/1994 Ivers et al. ................... 600/340
5,483,027 A * 1/1996 Krause .......................... 128/865
5,511,546 A * 4/1996 Hon .............................. 600/310
6,285,895 B1 * 9/2001 Ristolainen ........ A61B 5/14552
                                                          600/310

(Continued)

FOREIGN PATENT DOCUMENTS

JP       7-506497 A      7/1995
JP    2007-135718 A      6/2007

(Continued)

Primary Examiner — Eric Winakur
Assistant Examiner — Chu Chuan (JJ) Liu
(74) Attorney, Agent, or Firm — Hamre, Schumann, Mueller & Larson, P.C.

(57) ABSTRACT

The present invention provides a pulse oximeter of the portable type, which is possible to carry around and to use widely regardless of the adult, the infant, the newborn baby, and which can keep the finger still for performing the precise measurement. The pulse oximeter 100 comprises a measurement cavity 110 for accepting the examined portion (for example finger) of the subject, a measurement device 120 including a light emitting part 121 and a photo detecting part 122 facing between the measurement cavity 110, a filling element 140 formed from a material that the light used for the measurement can penetrate. The height and the curvature of the inner surface of the filling element 140 is larger than that of the outer surface of the filling element 140. The filling element 140 converts the height and the curvature of the inner space. The filling element 140 fills the gap space between the examined portion of the subject and the inner space of the measurement cavity 110, wherein the examined portion of the subject is pressed by the filling element 140 so as not to move freely in the measurement cavity.

13 Claims, 11 Drawing Sheets

(56) References Cited

U.S. PATENT DOCUMENTS

| | | | |
|---|---|---|---|
| 2002/0156354 A1* | 10/2002 | Larson | 600/344 |
| 2003/0045784 A1* | 3/2003 | Palatnik | A61B 5/14552 600/323 |
| 2005/0228248 A1* | 10/2005 | Dietiker | 600/323 |
| 2008/0058622 A1* | 3/2008 | Baker | 600/344 |
| 2011/0054280 A1* | 3/2011 | Yin et al. | 600/324 |

FOREIGN PATENT DOCUMENTS

| | | |
|---|---|---|
| JP | 3142046 U | 6/2008 |
| WO | WO 93/13402 | 7/1993 |

* cited by examiner (a)

(b)

(a)

Light from the emitting part 121 : λ1, λ2

Light through the photo filter 122 : λ1, λ2

The filling element 140 has no slit function (b)

Light from the emitting part 121 : λ1, λ2

Light through the photo filter 122 : λ1, λ2

The filling element 140 has slit function, light λ1, λ2 is absorbed (a)

(b)

(c)

Set by pinching the housing softly

PULSE OXIMETER

TECHNICAL FIELD

This invention relates to a pulse oximeter for measuring a pulse rate and a blood oxyecoia saturation in the blood of a subject by a non-invasive approach. A pulse oximeter of the present invention can be applied as either the one-time use pulse oximeter type or the re-usable pulse oximeter type.

BACKGROUND ART

As the equipment which can measure a blood oxyecoia saturation in the blood of a subject, a pulse oximeter becomes popular. A pulse oximeter can measure the blood oxyecoia saturation in the blood of a subject by a non-invasive approach continuously. It is used widely from the newborn baby to the adult on the medical care scene. The pulse oximeter can be classified into the transparent type pulse oximeter and the reflective type pulse oximeter according to the difference of the principle of measurement and the structure. The pulse oximeter also can be classified into the one time use pulse oximeter and the re-usable pulse oximeter according to the intended-purpose and number of use times. Hereinafter, the re-usable and transparent type pulse oximeter is explained as an example of the conventional pulse oximeter.

The basic structure of the transparent type pulse oximeter comprises a red light LED, an infrared LED and a photo detector. The LED irradiates red light and an infrared light to the examined part of the subject, and the photo detector detects the light which penetrated without being absorbed through the biomedical tissue of the skin, the vein, the muscle, the bone and so on. It measures a blood oxyecoia saturation in the blood by the signal change. Because the oxyhemoglobin (the oxygenated hemoglobin) and the reduced hemoglobin (the deoxyhemoglobin) differ in the light absorption percentage, the transparent type pulse oximeter measures oxygen saturation percentage (SpO2) by irradiating two different wavelengths and observing light absorbed in the blood, and analyzing the static state and the component that changes in the time of the signal, and computing a rate with the hemoglobin quantity combining with oxygen in the arterial blood.

For example, portions such as a finger or an ear lobe are chosen as the examined portion for the pulse oximeter because these portions are easy to pinch by the measurement cavity in order to insert the examined portion of the subject in the measurement cavity between the LED and the photo detector to measure. When using the large-sized pulse oximeter which has a big measurement cavity on an infant, his arm or his leg is chosen as an examined portion. Here, when measuring the oxygen saturation percentage (SpO2) by the pulse oximeter, all the light received by the photo detector should be decreased in intensity by penetrating through the biomedical tissues of the examined portion. It is important to avoid receiving the irradiated light from the LED directly without the decrease in intensity by penetrating through biomedical tissues of the examined portion. If the irradiated light from the LED is received directly by the photo detector, the correct measurement of the oxygen saturation percentage (SpO2) cannot be performed.

DISCLOSURE OF THE INVENTION

The Problems to be Solved

A conventional pulse oximeter in the prior art is widely used regardless of the adult, the infant, the newborn baby, but the following problem is pointed out in the medical care field.

The first problem of the conventional pulse oximeter in the prior art is the problem that it is designed for the adult use not to suit an infant and a newborn baby, so it is not called as an universal design. The problem is remarkable especially in the pulse oximeter of the conventional transparent type.

In the case of the oxygen saturation percentage (SpO2) measurement by the pulse oximeter, it is necessary that the examined portion maintains a static status in the measurement cavity. The pulse oximeter is designed for fixing the examined portion of the examinee in the lightly pinched condition in the measurement cavity where the LED and the photo detector are installed.

In the case of the oxygen saturation percentage (SpO2) measurement by the pulse oximeter, it is preferable that the finger is chosen as the examined portion of the subject. In fact, a fingertip type pulse oximeter in which the examined portion is a fingertip is commonly seen. However, the size of the measurement cavity is designed according to the adult finger size, so it doesn't fit the infant finger and the newborn finger.

As explained above, when measuring, the all light received by the photo detector should be decreased in intensity level by penetrating through the biomedical tissues of the examined portion. It is important to avoid receiving the irradiated light from the LED directly without decreasing its level by penetrating through biomedical tissues of the examined portion.

However, the finger is a fine small portion and moves easily, and it cannot be expected for an infant and a newborn baby to keep his finger still. They will move the finger actively to resist the measurement. It is the well-known problem among the medical staff that error increases in the measurement result of the oxygen saturation percentage (SpO2) and the measurement must be redone many times.

The second problem of the conventional pulse oximeter in the prior art is the problem that most conventional pulse oximeter are of the big and fixed installation type and few conventional pulse oximeter are the small and portable. Actually, a small and the handy-type conventional pulse oximeter exists in the prior art, but it is difficult for downsizing the device size except for the pulse oximeter of the transparent type which is designed for the adult, and there are no appropriate conventional pulse oximeter for the infant and the newborn baby in the prior art. Therefore, there is no choice for the infant and the newborn baby to use the conventional reflective type pulse oximeter for the infant and the newborn baby in the prior art, other than the big and fixed installation type pulse oximeter, which is not suitable for medical staff to carry easily. In other words, it is necessary to take the infant and the newborn baby to the room where the reflective type pulse oximeter is installed on demand when the measurement becomes necessary, or it is necessary to bring the reflective type pulse oximeter to the treatment room beforehand. In addition, the cost will be increased to purchase a reflective type pulse oximeter for the infant and the newborn baby apart from a pulse oximeter for the adult.

It is an object of the present invention to provide a pulse oximeter of the portable type, which is possible to carry around and which is possible to use widely, and regardless of whether the subject is the adult, the infant, the newborn baby, can keep the finger still for performing the precise measurement.

Means for Solving the Problems

In order to achieve the above-mentioned object, the present invention of a pulse oximeter comprises; a housing including a first body and a second body separated from each other, an adjustment mechanism for adjusting the distance between the first body and the second body, a measurement mechanism including a light emitting part and a photo detecting part installed in the first body and the second body and facing each other, a measurement cavity formed as the gap between the first body and the second body facing each other, an inner space opening vertically when accepting the examined portion of the subject, the inner space closing vertically after setting the examined portion of the subject, further comprising a filling element formed form an elastic material that the light used for the measurement can penetrate, whose shape is curved shape, the curvature of a curved inner surface becoming larger than that of a curved outer surface and a thickness of the edge portion being thicker than that of the central portion, the filling element filling the gap space between the examined portion of subject and the inner space of the measurement cavity.

It is preferable that the filling element is made of an elastic material in a plate body with a curved shape, and the filling element changes the curvature of the curved surface of the inner space of the measurement cavity. The curvature of the curved inner surface becomes larger than that of the curved outer surface.

According to the above-mentioned configuration of the first invention of the pulse oximeter, it can be applied to a wide variety of size of the examined portion of a subject and used as a universal design from the adult to the infant and the newborn baby, and can keep either the infant finger or the newborn baby finger still for performing the precise measurement.

It is preferable that the material of the filling element can be selected according to the position in the filling element. For example, only the portion of the filling element corresponding to the light emitting part and the photo detecting part need be formed by the material that the light used for the measurement by the measurement device can penetrate, and the remainder of the filling element may be formed by the material which the light used for the measurement can be absorbed.

For example, base of the filling element is formed by the material that the light used for the measurement by the measurement device can penetrate, the portion of the filling element corresponding to the light emitting part and the photo detecting part is formed by the base material as it is, and the remainder of the filling element is reformed from the base material by adding the absorbing material absorbing the light used for the measurement.

According to the above-mentioned configuration of the pulse oximeter, only the light emitted from the LED, penetrating the biomedical tissue of the examined portion of the subject, received by the photo detector can be detected, and the filling element can work as a slit for blocking the light coming from the side by reflecting in the measurement cavity to the photo detector.

One example of the material of the filling element is an elastic material in a plate body with a curved shape. If the curved shape is a suitable shape to fit infant and newborn baby fingers and the thickness is a suitable thickness to fill and adjust the inner space of a measurement cavity fit to the adult finger size to the inner space of the measurement cavity suitable for the infant finger and the newborn baby finger, the inner space of the measurement cavity can be changed appropriately according to all examinees among the adult, infant and newborn baby as a universal design.

Other example of the material of the filling element is a protean putty material. If the filling element is made of a protean putty material, the filling element can change its form freely to fit all of infant and newborn baby fingers, and the inner space of the measurement cavity can be changed appropriately according to all subjects among the adult, infant and newborn baby as a universal design.

Effect of the Present Invention

According to the pulse oximater of the present invention, it can fit to the all subjects among the adult finger, the infant finger and the newborn baby finger corresponding to the size of the subjects finger as a universal design, and it is possible to use widely regardless of the adult, the infant, the newborn baby and can keep the finger still for performing the precise measurement.

DETAILED DESCRIPTION OF THE PREFERRED EMBODIMENT

Some embodiments of a pulse oximeter according to the present invention are described below with reference to the relevant drawing. The pulse oximeter can be classified into the transparent type pulse oximeter and the reflective type pulse oximeter according to the different principle of measurement and the structure, and the pulse oximeter also can be classified into the one time use pulse oximeter and the re-usable pulse oximeter according to the intended-purpose and number of use times. Hereinafter, the re-usable and transparent type pulse oximeter is explained as an example of the conventional pulse oximeter. Needless to add, the claims of the present invention include but are not limited to the application, configuration, or quantity shown in the following embodiments.

Embodiment 1

A schematic view of the pulse oximeter 100 is shown as an example of this embodiment 1. In this configuration, the examined portion of the subject is the finger.

The type of the pulse oximeter showing below is what is called the pinch type, which can expand the opening by turning around the axis, and the subject inserts his finger as the examined portion and the inserted finger is pinched for measurement.

Figure 1:
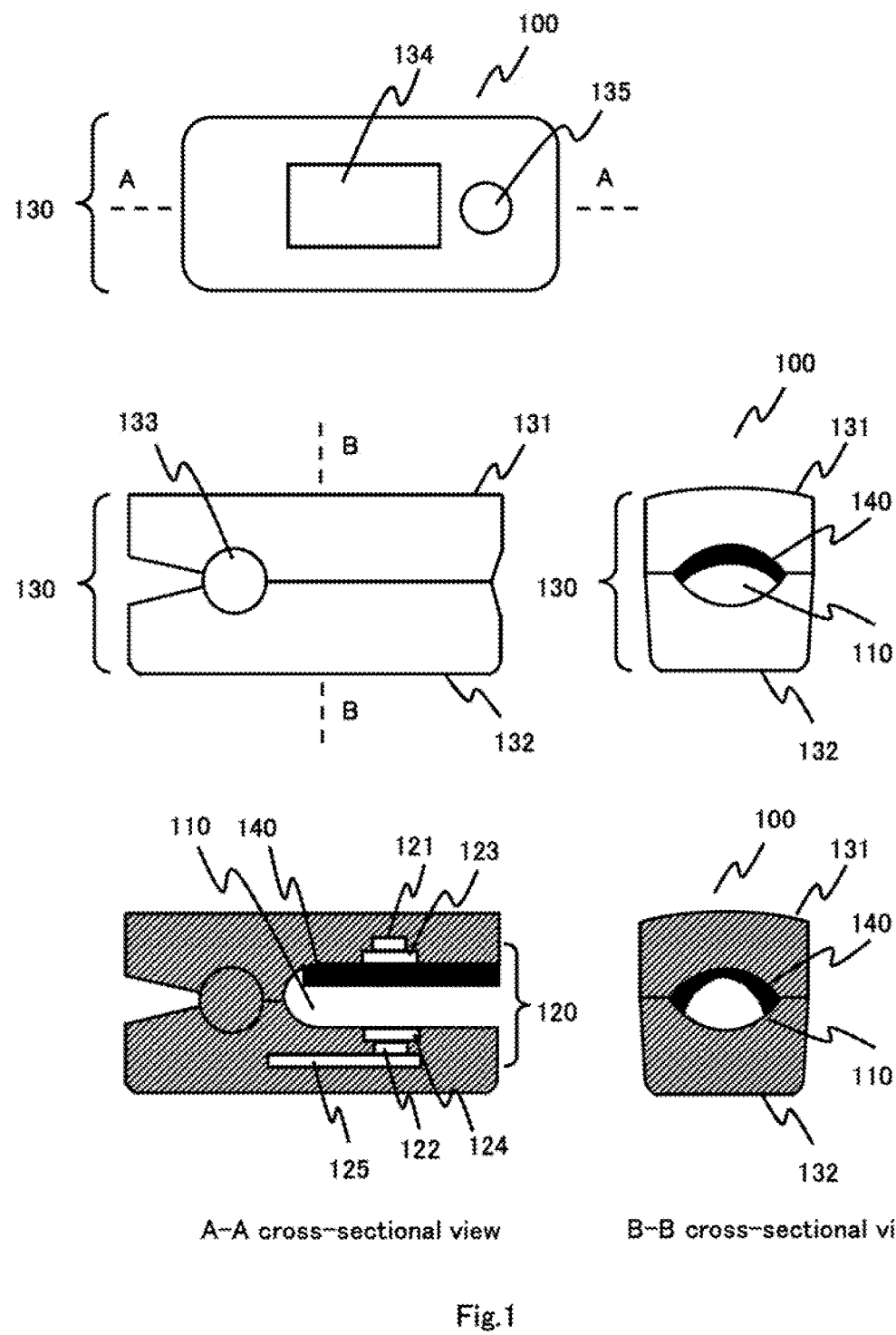
FIG. 1 is a schematic view of the pulse oximeter 100 in embodiment 1.

FIG. 1 is a schematic view of the pulse oximeter 100 in embodiment 1. In FIG. 1, the plane view, the left side view, the front view and the cross-sectional view showing mainly the measurement mechanism 120.

As shown in FIG. 1, the pulse oximeter 100 of the present invention includes the measurement cavity 110, the measurement mechanism 120, the housing 130, and the filling element 140.

The measurement cavity 110 is a space for accepting the examined portion of the subject. It includes the inner wall whose shape approximates the shape of the examined portion. Here, the examined portion is a finger (for example, middle finger of the right hand), and both the upper inner surface shape and lower inner surface shape of measurement cavity 110 are formed as an arch type surface, the height and the width of which are adjusted to fit to the adult finger. As the example, the width is about 8-10 mm, the height is about 2-3 mm, the radius of curvatures is about 13-15, and the depth is 25-40 mm.

The measurement cavity 110 may be the simple one body cavity bored in the housing. In this configuration, as shown in FIG. 1, the upper inner surface of the measurement cavity 110 is formed by the lower surface of the first housing 131 of the housing 130, and the lower inner surface of the measurement cavity 110 is formed by the upper surface of the second housing 132. The measurement cavity 110 is formed as the gap between the facing first housing 131 and second housing 132. In this configuration, both the upper inner surface and the lower inner surface are an arch shape curved surface, so the inner surface shape of the measurement cavity is easy to fit to the finger shape.

A diffuser panel 123 of the light emitting part 121 of the measuring mechanism 120 and a photo filter 124 of the photo detecting part 122 are provided at the inner surface of the measurement cavity 110.

Next, the measurement mechanism 120 is described below.

The measurement mechanism 120 comprises a light emitting part 121, a photo detector 122, a diffuser panel 123, a photo filter 124 and a signal controller 125.

The light emitting unit 121 is the part that includes plural light sources and emits the plural light beam used in the measurement.

A device whose wavelength-selectivity is excellent may be employed as the light source, and for example, a LED may be employed. Hereinafter, the two LEDs with peak luminous wavelength of $\lambda 1$ and $\lambda 2$ (for example, 630 nm and 900 nm waveband areas) are employed as the light sources. As described later, light with peak luminous wavelength $\lambda 1$ and the light with peak luminous wavelength $\lambda 2$ are emitted alternately from the light emitting part 121 by the control of signal control part 125.

It is preferable that the diffuser panel 123 is installed for the light emitting part 121. The diffuser panel 123 is the optical device that changes the light from the point source emitting light into the surface emitting light, and the diffuser panel 123 is installed as covering the front surface of the light sources. For example, the diffuser panel 123 is made from a transparent polystyrene resin or an acryl resin.

The two LEDs cannot help but being two parts physically, even if they are arrayed near to each other. Therefore, there is the light path difference between the two light from each LED to the photo detector 122. This light path difference gives an influence on the measurement accuracy as the error. Therefore, the diffuser panel 123 is inserted in order to reduce the error caused by the light path difference for changing the light from the light source emitting light to the surface emitting light. As shown above, the diffuser panel 123 can reduce the error caused by the light path difference.

It is preferable that the antimicrobial protection be provided for the diffuser panel 123 beforehand when it is exposed at the inner surface and touches the examined portion of the subject directly.

The photo detector 122 includes plural photo detector elements and it is the element for detecting the light used for the measurement.

For example, the photo detector element may be a photo diode. For example, the photo diode whose sensitivity is adjusted high for the wavelengths $\lambda 1$ and $\lambda 2$ (for example, 630 nm and 900 nm waveband areas) is desirable.

The photo filter 124 is installed in front of the photo detector element and works as the light filter passing only the light in the pass wavelength range. It blocks the light except the pass wavelength range and reduces the sunlight level and illumination light level. The measurement cavity is a cavity for blocking the light from the surrounding environment from reaching the inner space. Therefore it is important to reduce the influence of the surrounding light coming from the gap between the opening and the examined portion of the examinee (the finger). The photo filter 124 is useful for receiving selectively the light emitted from the photo emitting element and passed through the examined portion of the subject, and the sunlight and the illumination light can be blocked effectively.

It is preferable that the antimicrobial protection is provided for the photo filter 124 beforehand if it is exposed at the inner surface and touches the examined portion of the subject directly.

The signal controller 125 is an element for controlling the processing of each component of the pulse oximeter, including the electronic circuit necessary for the signal processing to compute oxygen saturation percentage based on the signal detected by the photo detector 122.

The signal controller 125 controls the light emitting part 121 for emitting the light with wavelength $\lambda 1$ (630 nm) and the light with wavelength $\lambda 2$ (900 nm) alternately, controls the photo detector 122 for detecting the light passing through the biomedical tissue of the examined portion of the examinee, and detects the change value of the passing light in two waveband areas $\lambda 1$ (630 nm) wavelength and $\lambda 2$ (900 nm) wavelength in the signal caused by the pulsation of the blood, and then computes the ratio between the change values as the oxygen saturation percentage (SpO2), which is the absorbance ratio between an oxygenated hemoglobin and deoxyhemoglobin in the arterial blood.

The signal processing to compute the oxygen saturation percentage (SpO2) is not specifically limited as shown above. Other signal processing can be applied appropriately.

Next, the housing 130 is described below.

The housing 130 includes a first housing 131, a second housing 132 and an adjustable mechanism 133.

The outer form of the first housing 131 and the second housing is not specifically limited but they are arranged as facing each other via the adjustable mechanism 133. The arrangement of the first housing 131 and the second housing 132 is not limited, and in the example shown in FIG. 1, the first housing 131 is located at the upper side and the second housing 132 is located at the lower side.

There is an arch shape space in the lower surface of the first housing 131 and it forms the upper surface of the measurement cavity 110. There is an arch shape space in the upper surface of the second housing 132 and it forms the lower surface of the measurement cavity 110. As shown above, the measurement cavity is provided as the gap between the first housing 131 and the second housing 132.

In this example, the button 135 for selecting the measurement mode and the display 134 for displaying measurement results such as the oxygen saturation percentage (SpO2) and the pulse frequency are arrayed in the upper surface of the first housing 131. In this embodiment, the display 134 displays the oxygen saturation percentage (SpO2) and the pulse frequency.

The adjustment mechanism 133 adjusts the distance between the first housing 131 and the second housing 132. In this configuration, the adjustment mechanism 133 is installed as the hinge part connecting the first housing 131 and the second housing 132.

Figure 2:
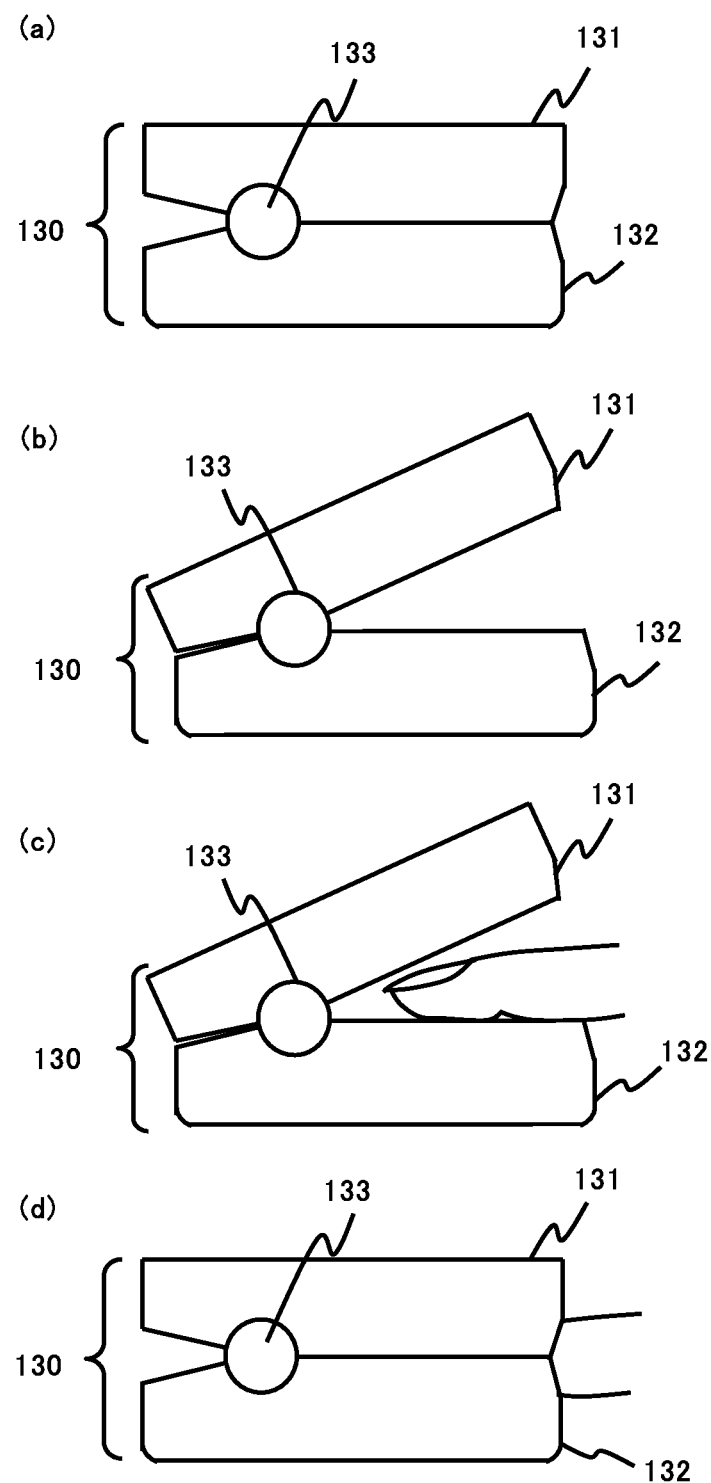
FIG. 2 is a schematic view showing the motion of the pulse oximeter 100.

FIG. 2 is a schematic view showing the motion of the pulse oximeter 100.

The pulse oximeter 100 shown here is an example employing the mechanism by which the first housing 131 and the second housing 132 can move from the basic position facing each other in parallel to the open position by moving up and down relative to each other with the adjustment mechanism as the axis by pinching the terminal end of the first housing 131 and the second housing 132 as shown in FIG. 2(a) to FIG. 2(b).

In the opening position shown in FIG. 2(b), the opening of the measurement cavity 110 is enlarged and the inner space of the measurement cavity 110 is expanded, so the measurement cavity 110 can accept the finger as the examined portion of the subject. After accepting the finger as the examined portion of the subject as shown in FIG. 2(c), and the measurement cavity 110 returns to the basic position as shown in FIG. 2(d), the opening of the measurement cavity 110 becomes narrow and the inner space of the measurement cavity 110 becomes narrow, so the measurement cavity 110 becomes a suitable space for measurement by blocking the sunlight and illumination light even if the finger as the examined portion is inserted in it.

Figure 3:
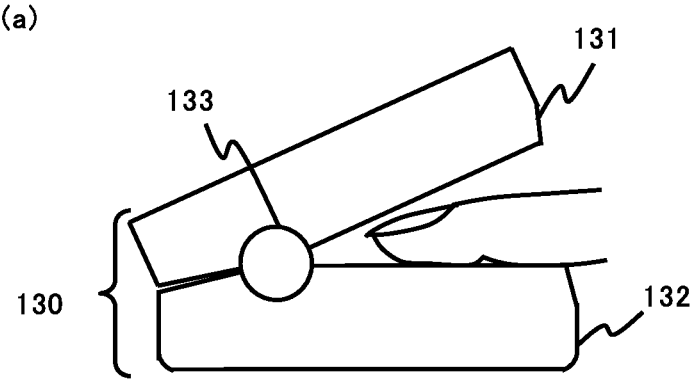
FIG. 3 is a schematic view showing the hinge structure of the adjustable mechanism 133 separating the axis and the bearing by elastic body 136 and the axis can be expanded vertically.
Figure 3:
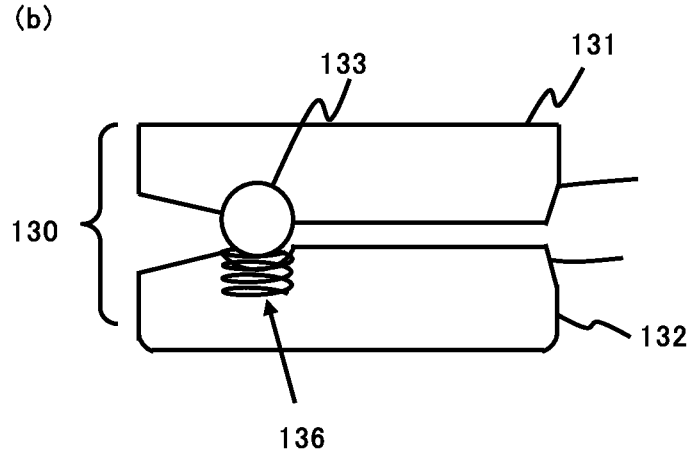

It is possible to expand the distance between the axis and the bearing by installing the elastic element 136 such as the spring in the hinge structure of the adjustment mechanism 133. FIG. 3 is the schematic view showing the hinge structure of the adjustable mechanism 133 separating the axis and the bearing by elastic body 136 and the axis can be expanded vertically. As shown in FIG. 3, the adjustment mechanism 133 has the margin for expanding vertically, so the measurement cavity 110 can accept the large and thick finger of the adult. In this example as shown in FIG. 2, the pulse oximeter is what is called the clip type for opening and closing the opening by using the adjustment mechanism 133 as the axis. Other mechanisms for opening and closing the opening by the adjustment mechanism 133 also can be applied. For example, the mechanisms can be for changing the distance between the first housing 131 and the second housing 132 by shifting the first housing 131 and the second housing 132 in parallel to each other.

Next, the filling element 140 is described.

The filling element 140 fills the gap space between the examined portion of subject and the inner space of the measurement cavity, and the filling element 140 presses the examined portion of the subject (finger) so as not to move freely in the measurement cavity. The measurement cavity of the pulse oximeter in general use, not in special use for the infant or the newborn baby, is designed for fitting the adult finger, so it does not fit to the finger of the infant or the newborn baby. In addition, the finger of the infant or the newborn baby is very small and moves freely, it is difficult to keep it still in the measurement period intentionally. Therefore, the filling element 140 presses the finger of the infant and the newborn baby so as not to move freely in the measurement cavity by filling the gap between the inner space and the finger.

The material selected for the filling element 140 is the material that passes the light with the wavelength $\lambda 1$ and the light with the wavelength $\lambda 2$ used for the measurement. The elastic material is preferable for pinching the finger of the infant and the newborn baby softly. For example, silicone is the preferable material.

The shape of the filling element 140 is the plate body with the curved shape in order to fit the finger of the infant and the newborn baby easily.

Figure 4:
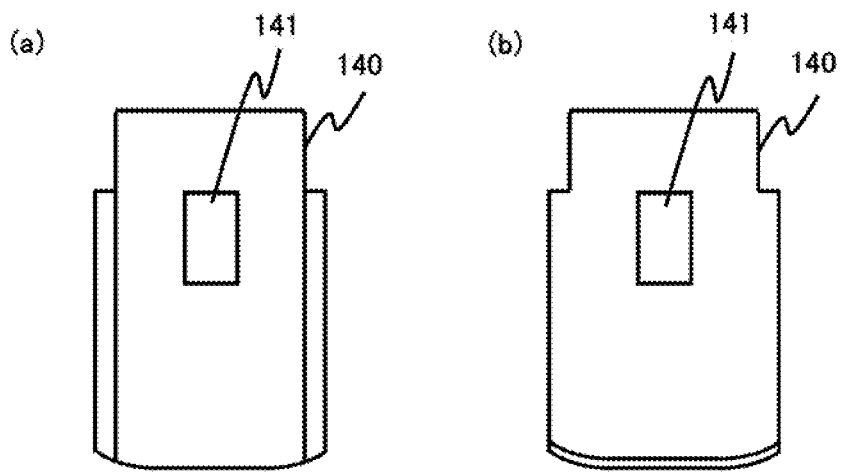
FIG. 4 is a schematic view showing the outer shape of the filling element 140 in embodiment 1.
Figure 4:

FIG. 4 is a schematic view showing the outer shape of the filling element 140. The filling element 140 is shown in enlarged size compared with that of the pulse oximeter 100 shown in FIG. 1.

FIG. 4(a) is the front view, FIG. 4(b) is the back view, and FIG. 4(c) is the horizontal cross-sectional view.

The curvature of the filling element 140 is described. In the filling element 140 as shown in FIG. 4(c), the curvature of the curved inner surface becomes larger than that of the curved outer surface. The curvature of the outer surface of the filling element 140 fits to the curvature of the inner surface of the measurement cavity 110, but the curvature of the inner surface of the filling element 140 is larger than it. The example shown in FIG. 4, the curvature of the outer surface of the filling element 140 is R=10, the curvature of the inner surface of the filling element 140 is R=13.4. Regarding the thickness, the thinnest portion is 1 mm. As shown above, the filling element 140 works as the converter element for converting the curvature and the height of the inner space in the measurement cavity 110.

The filling element 140 limits the degree of freedom of the inner space of measurement cavity 110 to be small and adjusts the inner space for pressing the finger of the infant and the newborn baby softly.

Next, the window 141 of the filling element 140 is described. As shown in FIG. 4(a), the window 141 is installed in the filling element 140 in this embodiment 1. The window 141 is installed at the position corresponding to the position of the light emitting part 121 and the photo detector 122 in the filling element 140. In other words, the window 141 is installed in the position where the light passes from the light emitting part 121 to the photo detector 122.

The material of the window 141 is a material (for example silicone) that passes the light with the wavelength $\lambda 1$ and the light with the wavelength $\lambda 2$ used for the measurement, which is the same as that of the base of the filling element 140. On the other hand, the material of the rest part of the window 141 is made of a material that includes an absorber that absorbs the light with the wavelength $\lambda 1$ and the light with the wavelength $\lambda 2$, or the rest part of the window 141 is coated with the absorber that absorbs the light with the wavelength $\lambda 1$ and the light with the wavelength $\lambda 2$.

As shown above, the rest part of the window 141 can absorb the light with the wavelength $\lambda 1$ and the light with the wavelength $\lambda 2$, so the window 141 of the filling element 140 can work as the slit that can block the outer light coming from the gap between the infant finger or the newborn baby finger, reflecting the inner wall of the measurement cavity 110 and reaching the photo detector.

Figure 5:
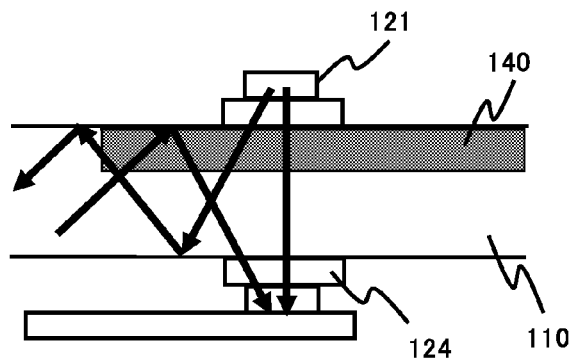
FIG. 5 is a schematic view showing the effect of the combination of the photo filter 124 of the photo detector 124 and the slit function of the window portion 141.
Figure 5:
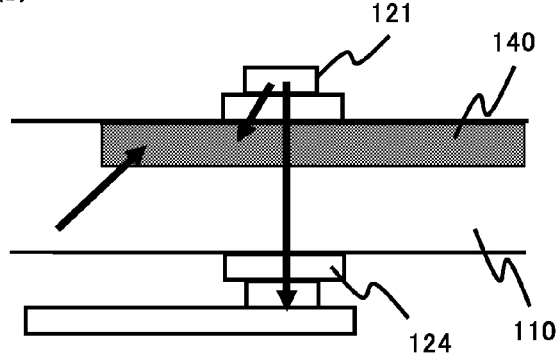

FIG. 5 is the figure which explains the effect achieved by the combination of the photo filter 124 of the photo detector 122 and the slit of the window part 141. FIG. 5(a) shows the effect achieved by the photo detector 122 of the photo filter 124 only, FIG. 5(b) shows the effect achieved by the combination of the photo filter 124 of the photo detector 122 and the slit of the window part 141.

In FIG. 5(a) and FIG. 5(b), the photo filter 124 is installed to cover the photo detector 122, the light with the wavelength $\lambda 1$ and the light with the wavelength $\lambda 2$ is blocked in both cases, so the light with the wavelength $\lambda 1$ and the light with the wavelength $\lambda 2$ received by the photo detector are decreased. However, if the window 141 does not work as the slit and the rest of the window part 141 passes the light with the wavelength $\lambda 1$ and the light with the wavelength $\lambda 2$ as shown in FIG. 5(a), the light with the wavelength $\lambda 1$ and the light with the wavelength $\lambda 2$ included in the outer environmental light can go through the window part 141 or the rest part and the photo filter 124, so the photo detector receives the outer environmental light other than the light coming from the light emitting part 121 through the finger directly. On the other hand, as shown in FIG. 5(b), if the window 141 works as the slit function, the light with the wavelength $\lambda 1$ and the light with the wavelength $\lambda 2$ included in the outer environmental light is absorbed by the rest of the window part 141, only the light coming from the emitting part 121 through the finger is detected by the photo detector as shown in FIG. 5(b). As shown above, the slit function of the window 141 improves the oxygen saturation ratio accuracy detected by the pulse oximeter of the present invention.

Next, the replaceablity of the filling element 140 is described. The filling element 140 presses the examined portion of the subject (finger) so as not to move freely in the measurement cavity, but the size of the infant finger and the newborn baby finger is so different so that one piece of the filling element 140 cannot cover all the infant and newborn baby fingers. Therefore, it is preferable that the filling element 140 is replaceable to select the thickness according to the size of the finger of the subject such as the infant and the newborn baby. In the example shown in FIG. 4, the cut fit to the side shape of the measurement cavity 110 is provided on the side of filling element 140 in order to fit the filling element 140 to the measurement cavity 110 easily, so the filling element 140 is replaceable in the measurement cavity 110.

Figure 6:
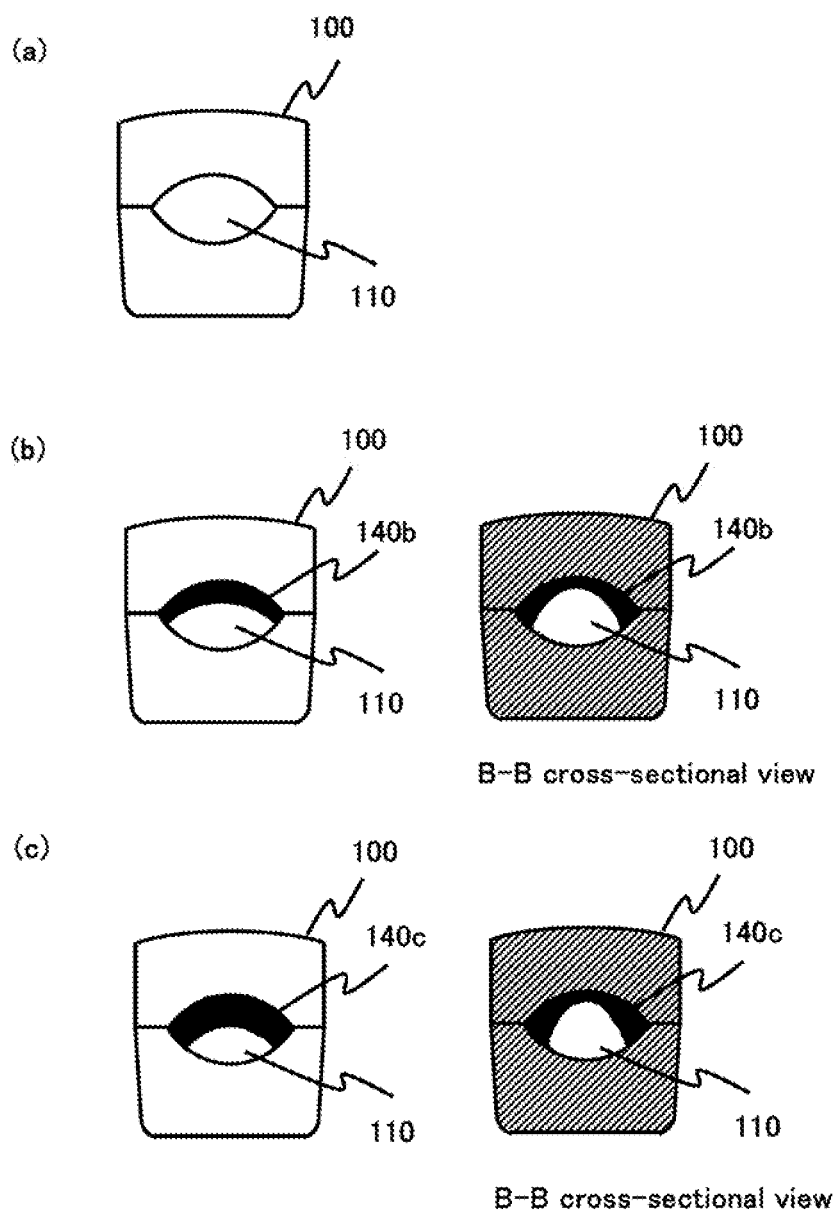
FIG. 6 is a schematic view showing the procedure for adjusting the inner space of the measurement cavity 110 by replacing the filling element 140.

FIG. 6 shows the figure which the inner space of measurement cavity 110 is adjusted by exchanging the filling element 140. FIG. 6(a) shows the opening of the measurement cavity 110 when the filling element 140 is not inserted, FIG. 6(b) shows the opening of the measurement cavity 110 when the filling element 140 for the infant finger is inserted, and FIG. 6(c) shows the opening of the measurement cavity 110 when the filling element 140 for the newborn baby finger is inserted in. As shown in FIG. 6(a), without inserting the filling element 140, the default size of the inner space of the measurement cavity 110 is corresponding to the adult finger, but as shown in FIG. 6(b), when the filling element 140b corresponding to the infant finger is inserted in the measurement cavity 110, the inner space of the measurement cavity 110 become narrow and the inner space of the measurement cavity 110 is converted to the size fit for the infant finger. In the same manner, as shown in FIG. 6(c), when the filling element 140c corresponding to the newborn baby finger is inserted in the measurement cavity 110, the inner space of the measurement cavity 110 become more narrow and the inner space of the measurement cavity 110 is converted to the size fit for the newborn baby finger.

Next, the outline of the use procedure of the pulse oximeter 100 of the present invention is described.

Figure 7:
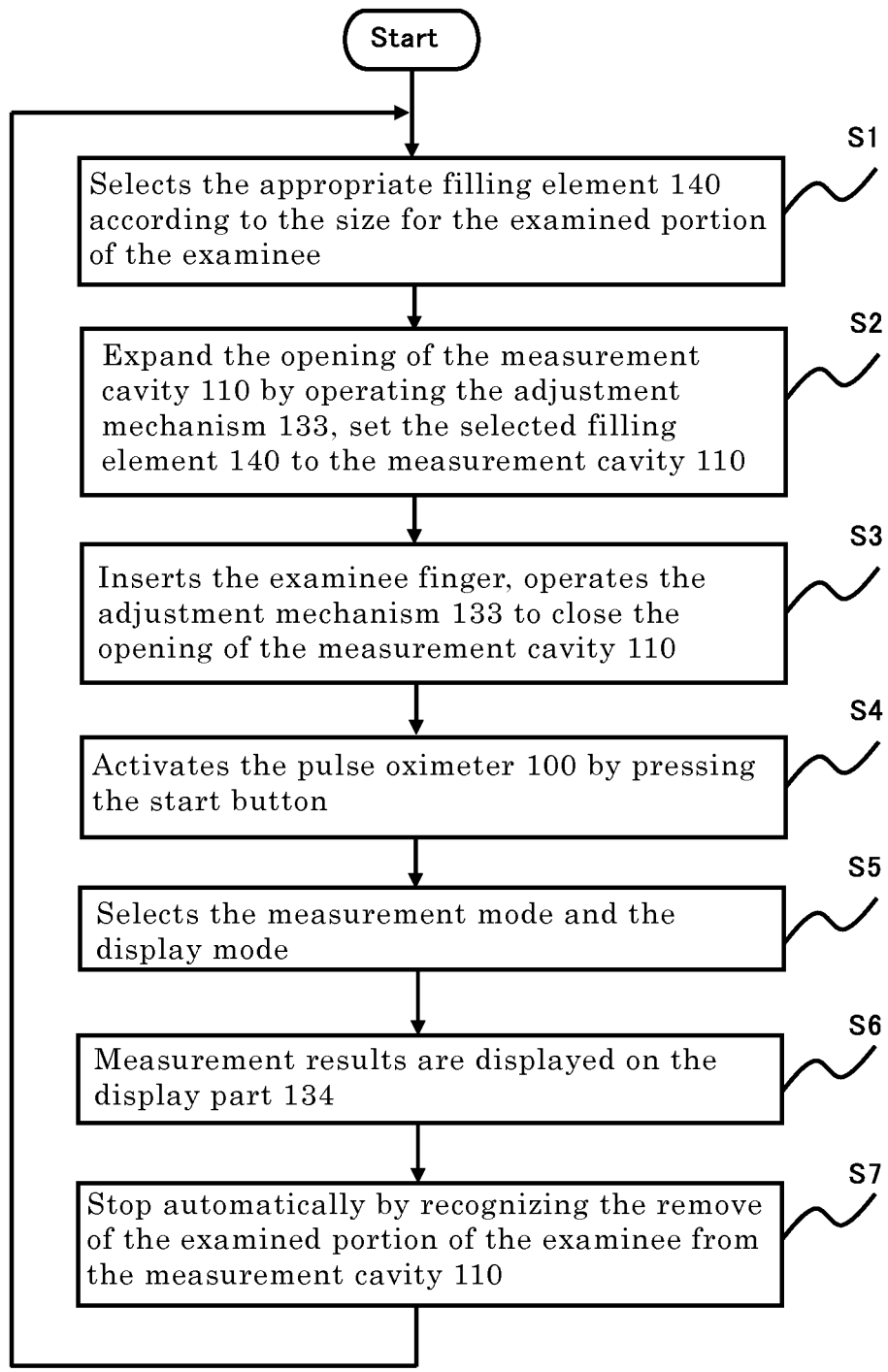
FIG. 7 is a flow chart showing the procedure for using the pulse oximeter 100 of the present invention.

FIG. 7 is a flowchart showing the use procedure of the pulse oximeter 100 of the present invention.

The pulse oximeter 100 of the present invention is of a very small and portable mobile type, and it is supposed that the medical staffs are always carrying the pulse oximeter in a pocket or are always hanging the pulse oximeter on the neck via a strap.

If the medical staff judges the necessity to measure the oxygen saturation percentage (SpO2) of the patient in the medical process or in the medical examination and he judges that the default size of the inner space of the measurement cavity 110 is not fit for the examined portion of the examinee such as the infant finger and the newborn baby finger, he selects the appropriate filling element 140 (Step S1). If there are several sizes of the filling elements such as the filling element for the infant finger (big size), the filling element for the infant finger (small size) and the filling element for the newborn finger, the pulse oximeter of the present invention can fit the examined portion of almost all subjects.

Next, the medical staff operates the adjustment mechanism 133 of the pulse oximeter of the present invention 100 to expand the opening of the measurement cavity 110, and set the selected filling element 140 to the measurement cavity 110 (Step S2). By inserting the filling element 140, the height and the curvature of the inner space are converted corresponding to those of the examined portion of the subject such as the infant finger and the newborn baby finger.

Next, the medical staff operates the adjustment mechanism 133 to expand the opening of the measurement cavity 110, inserts the subject finger such as the infant finger and the newborn baby finger and, operates the adjustment mechanism 133 to close the opening of the measurement cavity 110 (Step S3).

Next, the medical staff starts the measurement by operating the pulse oximeter 100 of the present invention adjusted by the filling element 140.

For example, the medical staff activates the pulse oximeter 100 by pressing the start button (Step S4), selects the measurement mode and the display mode (Step S5), and then the measurement will be started.

The measurement mechanism 120 of the pulse oximeter 100 of the present invention emits the light with the wavelength $\lambda 1$ and the light with the wavelength $\lambda 2$ from the emitting part 121 alternatively, and detects the light passed through the finger as the examined portion of the subject with the photo detector 122. The necessary processing for computing the oxygen saturation percentage (SpO2) and the necessary processing for computing the frequency of pulse are executed, and the measurement results are displayed on the display part 134 (Step S6).

Regarding the stop procedure, it may achieved by pressing the switch 135, but it also may achieved by the auto-judgment of the signal processor 125 by recognizing the removal of the examined portion of the subject from the measurement cavity 110 and recognizing the no signal of the frequency of pulse (Step S7).

As shown above, the basic structure and the basic procedure of the pulse oximeter 100 of the present invention are described, but various modifications can be possible. For example, the peak wavelengths of the light used in measurement are $\lambda 1$ and $\lambda 2$, but other peak wavelengths $\lambda 3$ and $\lambda 4$ of the light can be used together in the measurement in order to improve the measurement accuracy of the oxygen saturation percentage (SpO2). Moreover, the present invention can be applied to the complex-type pulse oximeter that can measure biomedical values other than the oxygen saturation percentage (SpO2) together with the oxygen saturation percentage (SpO2).

Embodiment 2

In this embodiment 2, the filling element of the pulse oximeter is made of a silicone putty material that can change its form freely, and the filling element is attached around the examined portion of the subject in the measurement procedure.

The pulse oximeter 100a of Embodiment 2 has the same configuration as the pulse oximeter 100 of Embodiment 1 except for the filling element 140a. In this Embodiment 2, the filling element 140a is described mainly.

Figure 8:
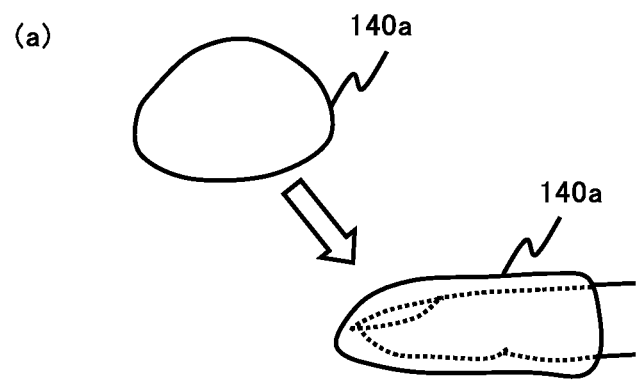
FIG. 8 is a schematic view showing the outer shape of the filling element 140a of the pulse oximeter 100a in embodiment 2.
Figure 8:
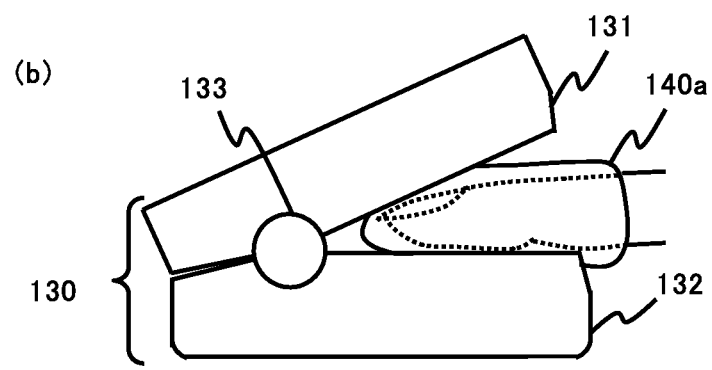
Figure 8:
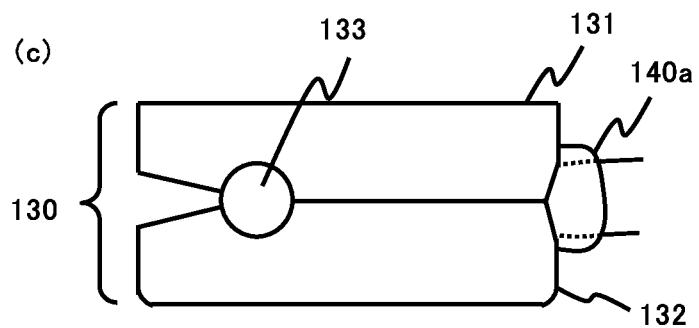

FIG. 8 shows the filling element 140a of the pulse oximeter 100a of Embodiment 2. The filling element 140a is made of a silicone putty material that can change its form freely, and the medical staff can deform the filling element 140a by hand according to the figure and size of the finger of the examinee and according to the inner space figure and size of the measurement cavity 110.

The material of the filling element 140a is the material that passes only the light with the wavelength λ1 (for example 630 nm) and the light with the wavelength λ2 (for example 900 nm) used for the measurement of the oxygen saturation percentage (SpO2), and which can change its form freely. For example, the gel resin material is preferable for the filling element because it is easy to treat and has high viscosity.

As shown in FIG. 8(a), the filling element 140a can be attached around the infant finger and the newborn baby finger easily.

Next, the use procedure of the pulse oximeter 100a of Embodiment 2 is described.

Figure 9:
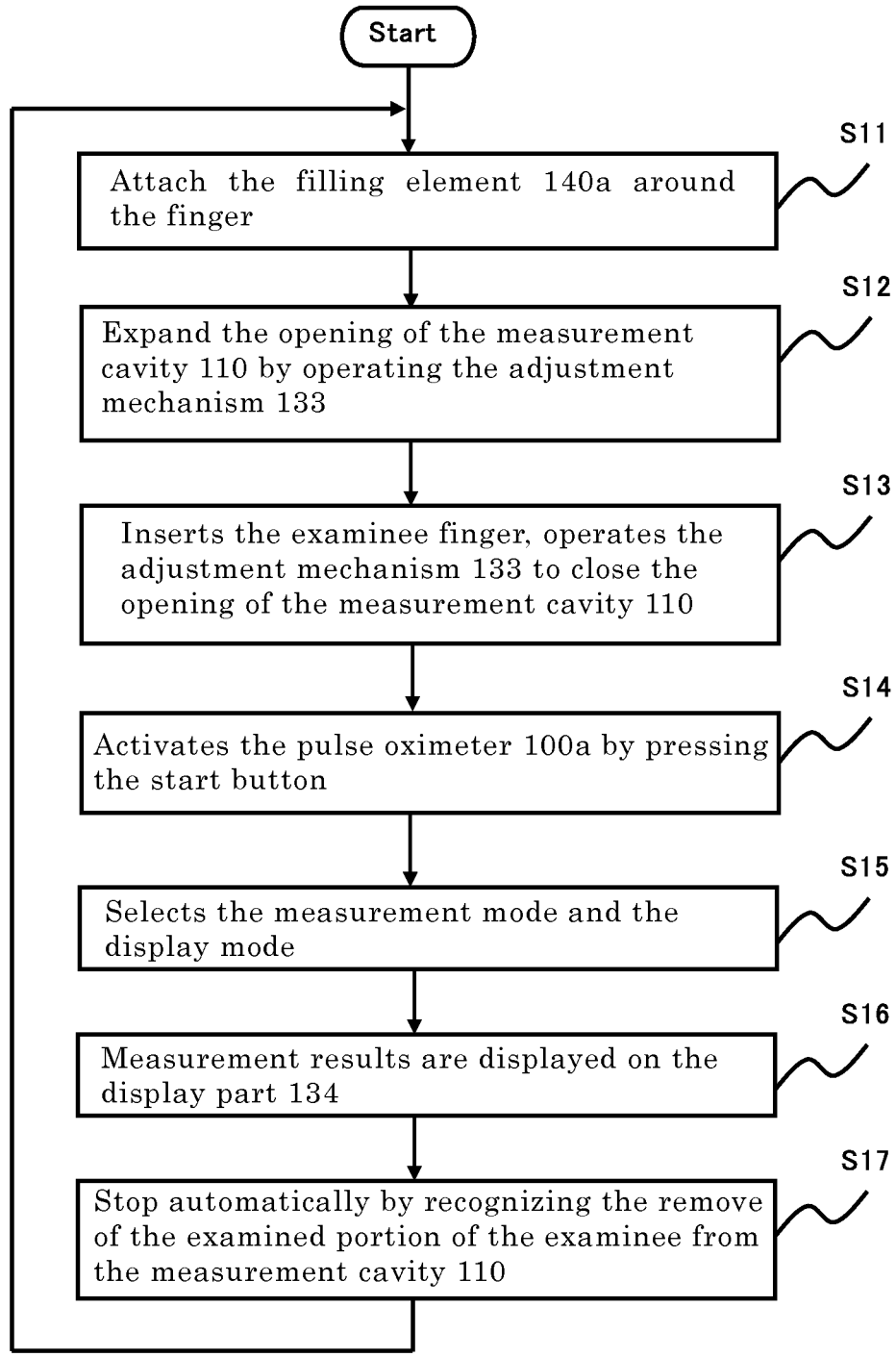
FIG. 9 is a flow chart showing the procedure for using the pulse oximeter 100a in embodiment 2.

FIG. 9 shows the flowchart explaining the use procedure of the pulse oximeter 100a of Embodiment 2.

First, the filling element 140a made of a silicone putty material is attached around the infant finger or the newborn baby finger as shown in FIG. 8 (Step S11 in FIG. 9).

Next, the medical staff operates the adjustment mechanism 133 of the pulse oximeter of the present invention 100a to expand the opening of the measurement cavity 110 (Step S12), sets the finger with the filling element 140a attached around, and closes the opening of the measurement cavity 110 by operating the adjustment mechanism 133 of the pulse oximeter. The form of the filling element 140a is deformed according to the inner space of the measurement cavity 110 and fits in the inner space of the measurement cavity 110 as shown in FIG. 8(c) (Step S13 FIG. 9). As shown above, it is important to fill the gap of the inner space of the measurement cavity and the examined portion of the examinee by deforming the filling element 140a freely.

Next, the medical staff will start the measurement by the pulse oximeter 100a with the filling element 140a. The following steps in the flowchart are the same as those in the flowchart shown in FIG. 7 of Embodiment 1. Therefore, the explanation is omitted.

Embodiment 3

The pulse oximeter 100b of Embodiment 3 is described. The housing is formed by the bag made from silicone. The finger of the examined portion is inserted in the bag when measuring.

Figure 10:
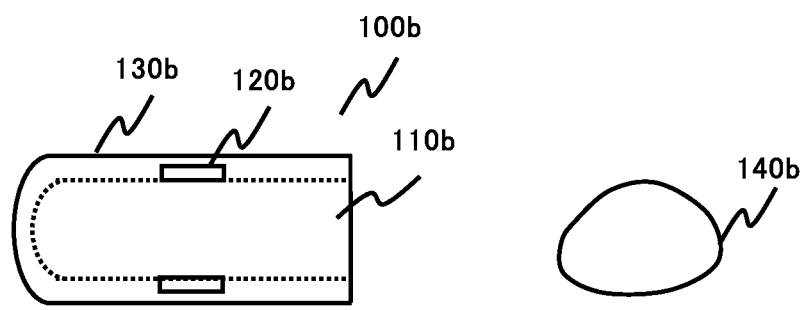
FIG. 10 is a schematic view of the pulse oximeter 100b in embodiment 3.
Figure 10:
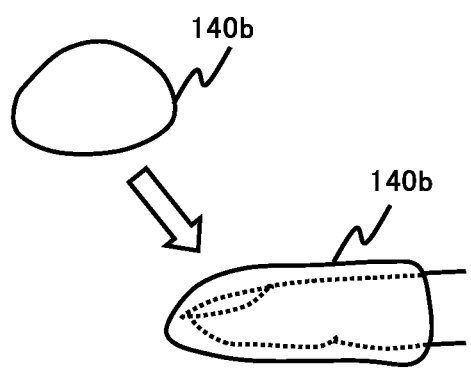
Figure 10:
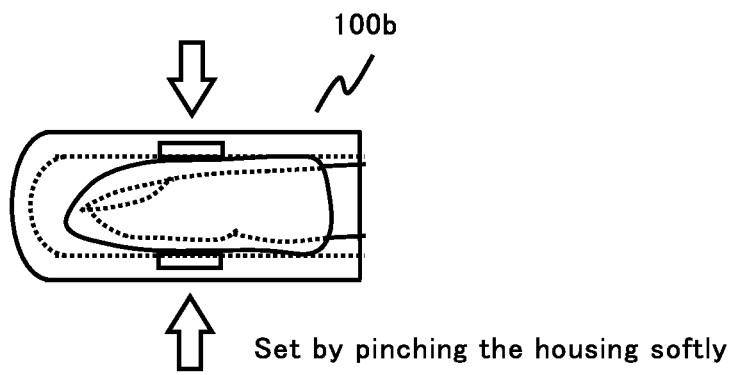

As shown in FIG. 10, the pulse oximeter 100b of Embodiment 3 comprises the measurement cavity 110b, the measurement mechanism 120b, the housing 130b and the filling element 140b. The buttons and displays are omitted in the FIG. 10 in order to describe the pulse oximeter 100b simply.

The housing 130b is a bag made from silicone, so the housing 130b has flexibility.

The measurement cavity 110b is provided as the inner space of the silicone bag, and it is cylinder shaped in this example. The silicone bag has flexibility, and the measurement cavity 110b is soft and elastic.

The basic configuration of the measurement mechanism 120b is the same as that of the measurement mechanism 120 shown in Embodiment 1. It is put in the bag 130b.

The filling element 140b is made of the clay type protean material, the same as the filling element 140a shown in Embodiment 2, it can deform freely by hand according to the form and size of the finger of the examinee and according to the inner space form and size of the measurement cavity 110.

Next, the use procedure of the pulse oximeter 100b of Embodiment 3 is described.

Figure 11:
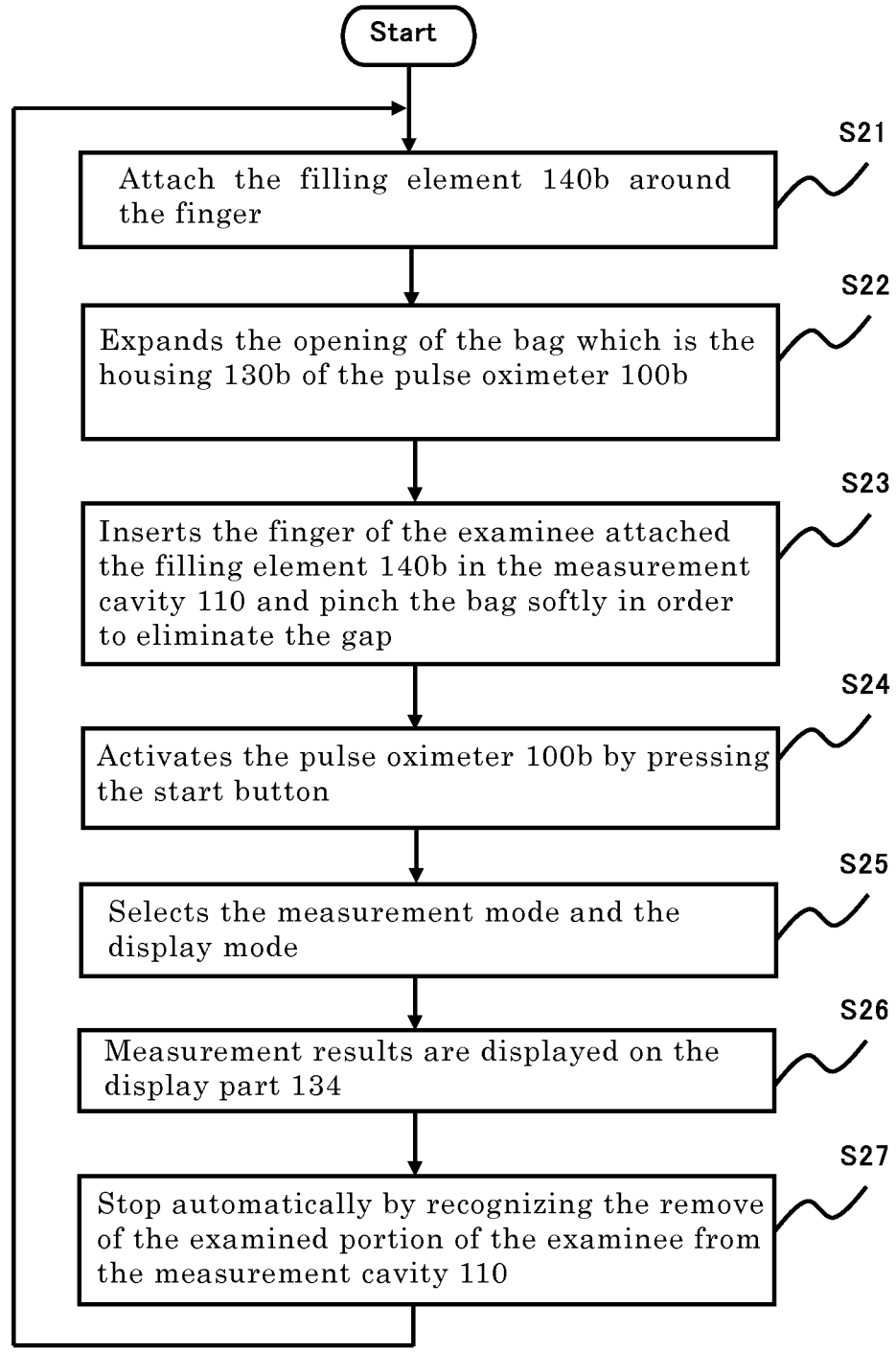
FIG. 11 is a flow chart showing the procedure for using the pulse oximeter 100b in embodiment 3.

FIG. 11 shows the flowchart explaining the use procedure of the pulse oximeter 100b of Embodiment 3 is described.

First, the filling element 140a made of a silicone putty material is attached around the infant finger or the newborn baby finger (Step S21 in FIG. 11).

Next, the medical staff expands the opening of the bag which is the housing 130b of the pulse oximeter 100b as shown in FIG. 10(b) (Step S22 in FIG. 11), inserts the finger of the examinee attached the filling element 140b in the measurement cavity 110 and pinches the bag softly in order to eliminate the gap space between the finger and the inner wall of the measurement cavity 110b. The shape of the filling element 140b deforms appropriately, so the inner wall of the measurement wall will be attached closely (Step S23 in FIG. 11). As shown above, both the shape of the housing 130b as the flexible bag and the shape of the filling element 140b are deformed together, the gap between the inner space of the measurement cavity and the examined portion of the examinee can be filled.

Next, the medical staff starts the measurement by using the pulse oximeter 100b employing the filling element 140b. The following steps in the flowchart are the same as those in the flowchart shown in FIG. 7 of Embodiment 1. Therefore, the explanation is omitted.

While some preferable embodiments of the pulse oximeter according to the present invention are described above, it should be understood that various changes are possible, without deviating from the technical scope according to the present invention. Therefore, the technical scope according to the present invention is limited only by the claims attached.

INDUSTRIAL APPLICABILITY

A pulse oximeter according to the present invention can be used extensively for measuring the oxygen saturation percentage and the pulse frequency by non-invasive operation.

The invention claimed is:
1. A pulse oximeter configured to receive an examined portion of a subject, comprising:
   a housing comprising a first body, and a second body movably joined to the first body to vary the distance between the first body and the second body;

a measurement mechanism including a light emitting part and a photo detecting part installed in the first body and the second body, respectively, and facing each other;

a measurement cavity having a first tactile surface formed on the first body and a second tactile surface formed on the second body, with the first and second tactile surfaces facing toward each other, the first and second tactile surfaces defining an elongate interior space having an axial direction in a length direction of the interior space, the first and second bodies being configured to move apart from each other in a direction transverse to the axial direction to an open position in which the interior space is enlarged for accepting an examined portion of an subject, and after the examined portion of the subject is placed in the measurement cavity, the first and second bodies being configured to move toward each other to an examination position in which the interior space is decreased relative to the open position, one of the first and second tactile surfaces being configured to have a first curvature when viewed from the axial direction, the first curvature being configured to grip an examined portion of a first size directly during measurement; and a curvature conversion element configured to be removably attached to the respective tactile surface that has the first curvature, the curvature conversion element having an outward facing surface that has a same curvature as the first curvature so that the outward facing surface of the curvature conversion element is attached to the respective tactile surface that has the same curvature, and an inward facing surface that has a second curvature when viewed from the axial direction, the second curvature being configured to grip an examined portion of a second size smaller than the first size directly during measurement; and wherein the curvature conversion element is configured to convert a curvature of the measuring cavity from the first curvature of the respective tactile surface to the second curvature of the inward facing surface of the curvature conversion element, wherein the curvature conversion element is configured to allow light emitted from the light emitting part to penetrate at least a portion of the curvature conversion element, wherein the second curvature is greater than the first curvature when the curvature conversion element is not deformed, such that when viewed from the axial direction a thickness of an edge portion of the curvature conversion element is greater than a thickness of a central portion of the curvature conversion element, wherein the light emitting part of the measurement mechanism is disposed within the first body between the first tactile surface and an outward facing surface of the first body opposite to the first tactile surface, and the photo detecting part of the measurement mechanism is disposed within the second body between the second tactile surface and an outward facing surface of the second body opposite to the first tactile surface, wherein when the pulse oximeter is used to measure the examined portion of the first size, the first tactile surface is in contact with a first side of the examined portion of the first size, and the second tactile surface is in contact with a second side of the examined portion of the second size, the first and second sides of the examined portion of the first size being opposed to each other, wherein when the pulse oximeter is used to measure the examined portion of the second size, and the curvature conversion element is attached to the first tactile surface, the inward facing surface of the curvature conversion element is in contact with a first side of the examined portion of the second size, and the second tactile surface is in contact with a second side of the examined portion of the second size, the first and second sides of the examined portion of the second size being opposed to each other, wherein when the pulse oximeter is used to measure the examined portion of the second size, and the curvature conversion element is attached to the second tactile surface, the first tactile surface is in contact with a first side of the examined portion of the second size, and the inward facing surface of the curvature conversion element is in contact with a second side of the examined portion of the second size, the first and second sides of the examined portion of the second size being opposing to each other, and wherein the pulse oximeter includes three surfaces, the first tactile surface, the second tactile surface and the inward facing surface of the curvature conversion element, that are contactable with the examined portion of a subject.

2. A pulse oximeter according to claim 1, wherein only the portion of the curvature conversion element corresponding to the light emitting part and the photo detecting part is formed from a material that passes the light used for the measurement by a measurement device, and the remained of the curvature conversion element is formed from a material configured to absorb the light used for the measurement.

3. A pulse oximeter according to claim 1, wherein the curvature conversion element is made of a silicone putty material.

4. A pulse oximeter according to claim 1, wherein the tactile surfaces of the first and second bodies of the housing constitute first and second inward facing surfaces of the measurement cavity, respectively.

5. A pulse oximeter according to claim 1, wherein the curvature conversion element is secured to the measurement cavity without adhesive.

6. A pulse oximeter according to claim 1, wherein the curvature conversion element is made of an elastic material that is configured to deform under pressure, a volume of the measurement cavity is converted from a first volume to a volume greater than the first volume when the curvature conversion element is deformed.

7. A pulse oximeter according to claim 1, wherein the curvature conversion element having a second curvature corresponding to the examined portion is selected from a plurality of pre-prepared curvature conversion elements, each of the plurality of pre-prepared curvature conversion elements having a different second curvature.

8. A pulse oximeter according to claim 1, wherein the curvature conversion element is configured to move from the tactile surface to which the curvature conversion element has been attached to allow the size of the measurement cavity to be defined by the first and second tactile surfaces directly.

9. A pulse oximeter according to claim 1, wherein the light emitting part of the measurement mechanism does not protrude beyond a portion of the first tactile surface that surrounds the light emitting part.

10. A pulse oximeter according to claim 1, wherein an inward facing side of the photo detecting part of the measurement mechanism does not protrude beyond a portion of the first tactile surface that surrounds the photo detecting part.

11. A pulse oximeter according to claim 1, wherein the first tactile surface has a smooth curvature.

12. A pulse oximeter according to claim 1, wherein the second tactile surface has a smooth curvature.

13. A pulse oximeter according to claim 1, wherein the curvature conversion element does not include a cavity that receives either the light emitting part or the photo detecting part.

* * * * *